(12) United States Patent
Islava (10) Patent No.: US 9,707,364 B2
(45) Date of Patent: Jul. 18, 2017

(54) METHOD AND APPARATUS FOR HOLDING ORAL AIRWAY DEVICES

(71) Applicant: Laerdal Medical AS, Stavanger (NO)

(72) Inventor: Steve Islava, Santa Ana, CA (US)

(73) Assignee: LAERDAL MEDICAL, AS, Stavanger (NO)

( * ) Notice: Subject to any disclaimer, the term of this patent is extended or adjusted under 35 U.S.C. 154(b) by 321 days.

(21) Appl. No.: 14/453,690

(22) Filed: Aug. 7, 2014

(65) Prior Publication Data

US 2016/0038703 A1  Feb. 11, 2016

(51) Int. Cl.
*A61M 16/04* (2006.01)

(52) U.S. Cl.
CPC ................................ *A61M 16/0497* (2013.01)

(58) Field of Classification Search
CPC ............ A61M 16/0488; A61M 16/049; A61M 16/0493; A61M 16/0497
USPC ......... 128/859, 861, 200.26, 201.26, 207.14, 128/207.15, 207.17, 207.18, DIG. 26; 604/77, 79, 174
See application file for complete search history.

(56) References Cited

U.S. PATENT DOCUMENTS

| | | | |
|---|---|---|---|
| 189,767 A * | 4/1877 | Mole ....................... | B25B 1/125 269/212 |
| 3,835,861 A * | 9/1974 | Kees, Jr. ................ | A61B 90/14 24/492 |
| 4,683,882 A * | 8/1987 | Laird ................ | A61M 16/0488 128/207.17 |
| 4,832,019 A * | 5/1989 | Weinstein ......... | A61M 16/0488 128/207.17 |
| 4,934,889 A * | 6/1990 | Kurosaki ............ | F16B 37/0842 411/267 |
| 5,097,827 A * | 3/1992 | Izumi ..................... | A61M 25/02 128/200.26 |
| 5,402,776 A * | 4/1995 | Islava ............... | A61M 16/0488 128/207.14 |

(Continued)

FOREIGN PATENT DOCUMENTS

KR  WO 2014062012 A1 *  4/2014  .......... A61M 5/1415

OTHER PUBLICATIONS

Machine translation of WO 2014062012 A1.*

(Continued)

*Primary Examiner* — Tan-Uyen (Jackie) T Ho
*Assistant Examiner* — Joseph D Boecker
(74) *Attorney, Agent, or Firm* — Kaplan Breyer Schwarz, LLP (57) ABSTRACT

A device for securing an oral airway device in place with a patient's oral cavity. The device comprises a V-clamp which is slid along its upper edge in the direction of the oral airway device. After making contact with the oral airway device with the V-clamp, the user may choose to manipulate a screw disposed on the device and bring its corresponding distal end into physical contact with the opposing surface or side of the oral airway device, thereby creating a compressive force on the oral airway device. Alternatively, the device may comprise a V-clamp on a first portion which is disposed on a sliding track. The first portion may be manipulated with the addition of a screw in order to create a compressive force on the oral airway device. Alternatively, the device may comprise two rotating portions coupled together via a pivot point.

10 Claims, 5 Drawing Sheets

(56) References Cited

U.S. PATENT DOCUMENTS

| | | | | |
|---|---|---|---|---|
| 5,513,633 | A * | 5/1996 | Islava | A61M 16/0488 128/207.14 |
| 5,806,516 | A * | 9/1998 | Beattie | A61M 16/0488 128/207.14 |
| 6,010,484 | A * | 1/2000 | McCormick | A61M 16/0488 128/DIG. 26 |
| 6,067,985 | A * | 5/2000 | Islava | A61M 16/0488 128/200.26 |
| 6,123,326 | A * | 9/2000 | Kleinbongartz | B25B 5/068 269/143 |
| 6,578,576 | B1 | 6/2003 | Taormina et al. | |
| 6,708,966 | B1 * | 3/2004 | Troudt | B25B 5/067 269/249 |
| 8,156,934 | B2 | 4/2012 | Trodler | |
| 8,360,063 | B2 | 1/2013 | Liland | |
| 8,636,008 | B2 | 1/2014 | Flory et al. | |
| 2002/0185800 | A1 * | 12/2002 | Duncan | B25B 1/103 269/242 |
| 2005/0110269 | A1 * | 5/2005 | Chu | F16L 41/12 285/24 |
| 2009/0229616 | A1 * | 9/2009 | Liland | A61M 16/0488 128/207.14 |
| 2010/0314517 | A1 * | 12/2010 | Patzer | A61M 5/1415 248/230.3 |
| 2011/0240034 | A1 | 10/2011 | Ciccone | |
| 2014/0238406 | A1 * | 8/2014 | Borre | A61M 16/0493 128/207.17 |
| 2015/0018759 | A1 * | 1/2015 | Velez-Rivera | A61M 16/0497 604/79 |
| 2016/0339194 | A1 * | 11/2016 | Molden | A61M 16/0497 |
| 2016/0361509 | A1 * | 12/2016 | Blessing, Jr. | A61M 16/0497 |

OTHER PUBLICATIONS

"First Office Action issued in counterpart Chinese Patent Application No. 2015-201684874", Jun. 18, 2015, Publisher: CIPO, Published in: CN.

"International Search Report and the Written Opinion of the International Searching Authority", dated Oct. 7, 2015, issued in counterpart International Patent Application No. PCT/US2015/039493.

* cited by examiner

METHOD AND APPARATUS FOR HOLDING ORAL AIRWAY DEVICES

BACKGROUND

Field of the Technology

The disclosure relates to the field of medical and paramedic support devices, and more particularly, to adjustable holders for accommodating various endotracheal airway devices.

Description of the Prior Art

Endotracheal tubes or other oral airway devices have long been used to clear the airway of a patient and provide them with a means of breathing when they are unconscious due to having gone under general anesthesia, having been involved in an accident, or for any number of other medical related reasons. Typically, oral airway devices are comprised of plastic and come in a variety shapes and sizes that are tailored to fit specific needs or tasks. An endotracheal tube is a catheter which is inserted through the nose or mouth of the patient and then down into the trachea. The tube provides a semi-rigid structure which holds open the patient's airway while they are unconscious, permitting them to breathe. Other oral airway devices include mask ventilators and supraglottic airway devices which also provide the patient sufficient means for breathing in an emergency medical situation.

Regardless of which oral airway device is used however, in order to function correctly the oral airway device must be inserted or placed correctly if the patient is to have any chance of success. Any patent airway which is created, either by the oral airway device itself or by a secondary device which is held in place by the oral airway device, may be robust enough to maintain an open airway, yet supple enough that it will not damage or cause injury to the patient who is receiving the oral airway device. This is particularly important in emergency situations where quick insertion of the oral airway device is crucial and may even be lifesaving. Additionally, not every patient requires the same treatment, therefore emergency response personnel such as paramedics must carry multiple different types of oral airway devices as a precaution for every situation they may encounter. Each device is slightly different however in terms of size or shape which increases the complexity of the medical assessment and treatment of the patient in a timely manner.

What is needed therefore is a supplemental device that is capable of accommodating a variety of different types and sizes of oral airway devices that is also quick to apply to the patient.

BRIEF SUMMARY

The invention includes a device for securing an oral airway device in the oral cavity of a patient. The device includes a mouth piece configured to fit over the mouth of the patient with an opening that is used to accommodate an oral airway device therein. A thumb screw is also included and is disposed on one of the edged of the opening within the mouth piece along with an adjustable compressive means disposed on another one of the edges of the opening. The adjustable compressive means disposed on a second edge in one embodiment comprises a sliding clamp with a "V" shaped ridge defined therein.

In one particular embodiment, the mouth piece includes a sliding half and a stationary half coupled to the sliding half. The adjustable compressive means disposed on the second edge of the opening in this embodiment comprises a "V" shaped ridge defined in the sliding half. The sliding half of the mouth piece includes a ratchet which interacts with a plurality of ridges that are disposed on a ratchet track that is coupled to the stationary half of the mouth piece. The sliding half of the mouth piece also has a plurality of track apertures, each of which are configured to accommodate a distal end of the ratchet track there through.

In another embodiment, the sliding clamp also has a release tab and is coupled to the second edge so that a distal portion of the release tab is temporarily accommodated within a plurality of serrated teeth disposed on the second edge as the sliding clamp traverses the second edge, similar to a zip tie. Specifically, the distal portion of the release tab and the serrated teeth are configured to prevent any opposing movement of the sliding clamp when the distal portion of the release tab and serrated teeth are in a nested position.

In yet another embodiment, the mouth piece includes a rotating half and a fixed half connected together through a pivot, a "V" shaped ridge additionally being defined in the rotating half.

In another embodiment of the invention the device further includes a number of eyelets disposed on the mouth piece which are used to accommodate a strap or other attaching means. The strap is then used to fix the mouth piece over the mouth of the patient. The compressive means may further include a bite block disposed on its rear surface.

The invention also includes a method for securing an oral airway device in the oral cavity of a patient. The method includes inserting the oral airway device into the oral cavity of the patient, placing a device comprising a mouth piece around the mouth of the patient with the oral airway device being located within an opening in the mouth piece, and then adjusting a movable portion of the mouth piece until contact is made with a surface of the oral airway device. After making contact a thumb screw is adjusted until contact is made with another surface of the oral airway device. A compressive force is then applied between a distal end of the thumb screw and the movable portion of the mouth piece, thus locking it in a secure position.

In one embodiment, the method step of adjusting a movable portion of the mouth piece until contact is made with a surface of the oral airway device includes sliding a clamp coupled to the mouth piece across an opening defined in the mouth piece and then making surface contact between the surface of the oral airway device and a "V" shaped ridge defined in the clamp. The sliding of the clamp across the opening defined in the mouth piece involves ratcheting a portion of a release tab disposed on the clamp over a plurality of serrated teeth disposed along an edge of the opening defined within the mouth piece and then preventing any movement of the clamp along the edge of the opening after surface contact has been made with the oral airway device.

In another embodiment, the method step adjusting a movable portion of the mouth piece until contact is made with a first surface of the oral airway device includes adjusting a sliding half of the mouth piece by moving it towards a stationary half of the mouth piece. In this embodiment, the sliding half has a "V" shaped ridge defined therein which makes surface contact with the oral airway device. Adjusting of the sliding half of the mouth piece includes ratcheting a ratchet disposed on the sliding half over a plurality of ridges that are disposed along a ratchet track which is coupled to the stationary half of the mouth piece. An end of the ratchet track is inserted into one of a plurality of track apertures defined in the sliding half of the mouth piece which prevents any movement of the sliding half along the ratchet track after surface contact has been made with the oral airway device.

In yet another embodiment, the method step of adjusting a movable portion of the mouth piece until contact is made with a surface of the oral airway device includes adjusting a rotating half of the mouth piece by rotating it towards a fixed half of the mouth piece. The rotating half has a "V" shaped ridge defined therein which makes surface contact with the surface of the oral airway device. The rotating half rotates around or about a pivot which couples the rotating half and the fixed half of the mouth piece together.

The method of the current invention further includes adjusting the fit of the mouth piece over the mouth of the patient by tightening an adjustable strap connected to either end of the mouth piece, inserting a bite block into the oral cavity of the patient, and also releasing the oral airway device from the mouth piece by breaking surface contact between the distal end of the thumb screw and movable portion of the mouth piece with the surface of the oral airway device.

Additionally, the invention includes a mouth piece for securing an oral airway device in the oral cavity of a patient which includes a sliding half, a stationary half, and an opening for accommodating the oral airway device, the size of which is defined by the position of the sliding half relative to that of the stationary half. The sliding half and the stationary half are removably coupled to each other and the sliding half further includes a "V" shaped ridge defined into its surface. The sliding half and the stationary half are removably coupled to each other by a ratchet coupled to the sliding half and a ratchet track coupled to the stationary half. The ratchet is configured to interact with the ratchet track and prevent any movement of the sliding half relative to the stationary half. Finally, the sliding half of the mouth piece includes a plurality of apertures for accommodating an end of the ratchet track.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

BRIEF DESCRIPTION OF THE DRAWINGS

FIG. 3 is a frontal view of the mouthpiece seen in FIG. 2 with the V-clamp and the distal end of the thumb screw compressing the oral airway device disposed there between.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
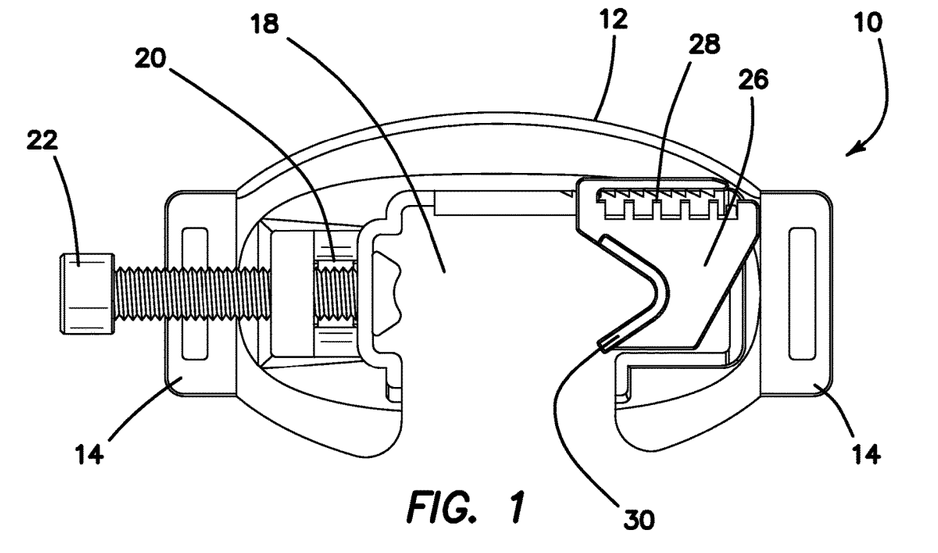
FIG. 1 is a frontal view of the mouthpiece of the current device with the V-clamp of the mouthpiece in the largest possible open position.

A first embodiment of the device is shown in FIG. 1 and is denoted generally by reference numeral 10. The device comprises a mouthpiece 12 which is substantially sized and shape to fit over the contours of the mouth of a patient. The mouthpiece 12 is preferably comprised of soft plastic and is layered with a soft padding material or foam on its reverse surface (not seen). Disposed on either end of the mouthpiece 12 is an eyelet 14 with a center hole defined therein. The eyelets 14 provide a means for a strap, belt, or other equivalent attaching means (not shown) to be coupled to the mouthpiece 12. The strap, belt, or other attaching means in turn provide a means for keeping the mouthpiece 12 affixed to the patient by wrapping the distal ends of the strap, belt, or other attaching means around the back of the head of the patient and then tightening the strap, belt, or other attaching means. In one embodiment, each eyelet 14 comprises its own strap, belt, or other attaching means which is threaded through the center hole of its respective eyelet 14 and then coupled thereto, preferably by folding over and attaching the proximal end of the attaching means to itself with a hook and latch fabric or other equivalent means. The mouthpiece 12 is then placed over the patient's mouth. The distal ends of each of the attaching means are then brought around the head of the patient and coupled to each other by means of a hook and latch fabric in order to provide a tight or snug fit around the patient's head with the mouthpiece 12 firmly in place over the patient's mouth. Alternatively, after placing the mouthpiece 12 over the patient's mouth, a single strap, belt, or other attaching means may be coupled to one of the eyelets 14, wrapped about the patient's head, and then coupled to the opposing eyelet 14 disposed on the opposing side of the mouthpiece 12.

Figure 6:
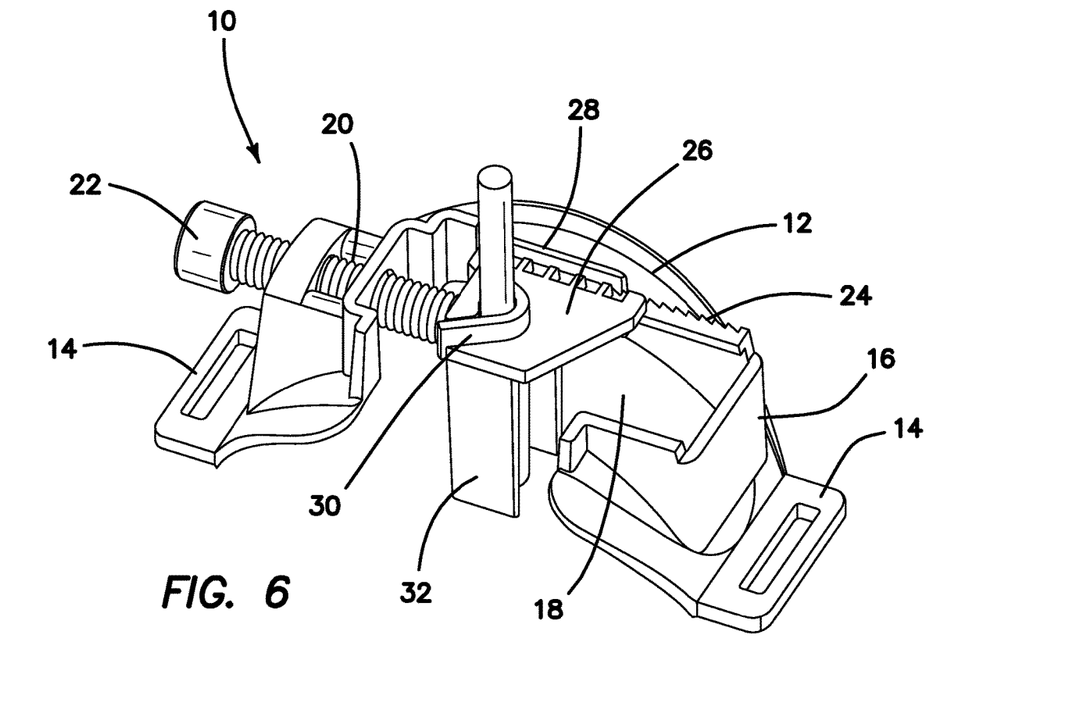
FIG. 6 is a perspective view of the mouthpiece seen in FIG. 4 and showing the bite block disposed on the rear surface of the V-clamp.

As best seen in the three quarter perspective view of FIG. 6, the mouthpiece 12 comprises a substantially raised portion 16 which itself comprises an opening 18 defined in the middle thereof. The opening 18 is wide enough to accommodate an oral airway device, or alternatively, a plurality of oral airway devices, with relative ease. The raised portion 16 also comprises an aperture 20 which accommodates an elongated screw 22 threaded therein. The screw 22 further comprises a distal end 34 configured to make surface contact with an inserted oral airway device. The opening 18 also comprises an upper edge 24 which itself comprises a serrated or notched surface as best seen in FIG. 6. Coupled to the upper edge 24 is a V-clamp 26. The V-clamp 26 is slidably disposed on the upper edge 24 via a releasable ratchet pawl 28 that interacts with the individual ratchet teeth of the upper edge 24 as discussed in further detail below. The V-clamp 26 also comprises a substantially V shaped flange 30 defined into the left hand edge of the V-clamp 26. As seen in FIG. 1, the V shaped flange 30 helps define a substantially triangular or "V" shaped cut out within one side of the V-clamp 26 used to accommodate oral airway devices 36 of various sizes and shapes. Additionally, as best seen in FIG. 6, the V-clamp 26 also comprises a bite block 32 coupled to the rear surface of the V-clamp 26 that may be placed inside the mouth of the patient in order to protect the patient's teeth and prevent any extraneous motion of the patient's tongue.

Figure 2:
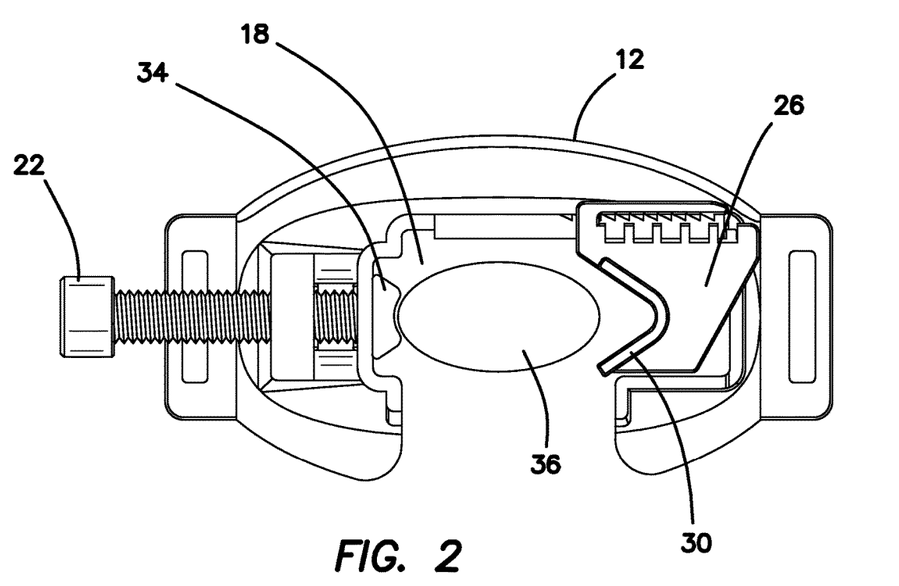
FIG. 2 is a frontal view of the mouthpiece seen in FIG. 1 with an oral airway device disposed between the V-clamp and the distal end of the thumb screw of the mouthpiece.
Figure 3:
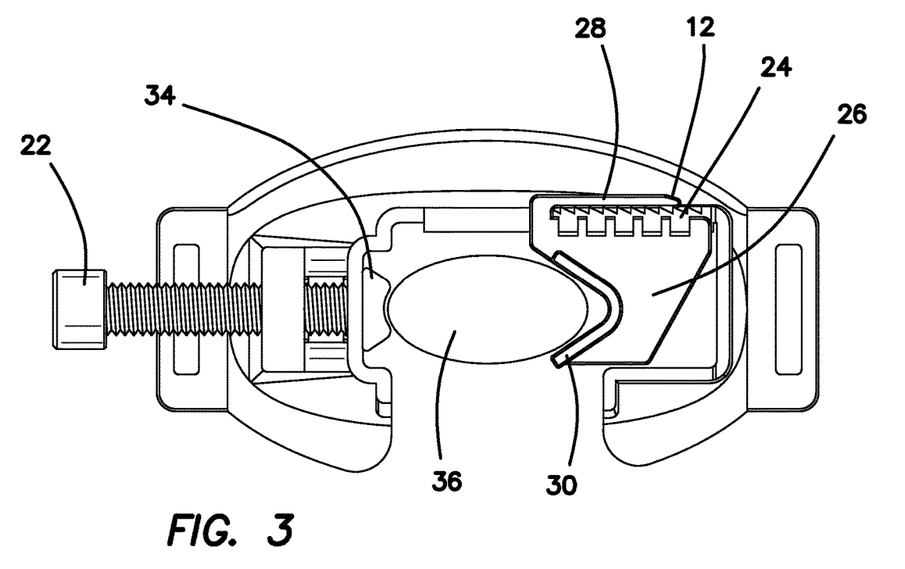

The use the device 10, the user places the mouthpiece 12 in close proximity of the patient's face and mouth. The user inserts an oral airway device, shown as a generic object and generally denoted with reference numeral 36 in FIG. 2, into the patient's oral cavity according to its prescribed use within the opening 18 of the mouthpiece 12, specifically between the V-clamp 26 and the distal end 34 of the screw 22. Alternatively, the user may first insert the oral airway device 36 into the patient's oral cavity, and then dispose the mouthpiece 12 around the oral airway device 36. With the oral airway device 36 and mouthpiece 12 in place, the user manipulates the V-clamp 26 by sliding it along the upper edge 24 in the direction of the oral airway device 36 as seen in FIG. 3. The user continues to slide the V-clamp 26 along the upper edge 24 until contact is made with the oral airway device 36. The V shaped flange 30 allows for a plurality of differently sized or shaped oral airway devices 36 to be accommodated by the V-clamp 26. In the various figures it is shown that a substantially oval shaped oral airway device 36 has been locked into position using the current device 10, however it is to be expressly understood that alternative oral airway devices 36 comprising shapes or sizes explicitly not shown within the figures may also be used with departing from the original spirit and scope of the invention. After making contact with the oral airway device 36 with the V-clamp 26, the user may choose to manipulate the screw 22 and bring its corresponding distal end 34 into physical contact with the opposing surface or side of the oral airway device 36. Alternatively, the user may decide to first adjust the screw 22 and bring the distal end 34 into contact with the oral airway device 36 before adjusting the V-clamp 26 as describe above. With the distal end 34 of the screw 22 and the V shaped flange 30 of the V-clamp 26 making contact with opposing edges or surfaces of the oral airway device 36, a compressive force is placed on the oral airway device 36 which firmly locks into position within the patient's oral cavity.

As the V-clamp 26 slides along the upper edge 24, the releasable ratchet pawl 28 passes over the serrated teeth or protrusions which define the surface of the upper edge 24. As is known in the art, the serrated teeth of the upper edge 24 and the releasable ratchet pawl 28 are defined and configured such that a distal portion of the releasable ratchet pawl 28 is temporarily accommodated or nested within each of the individual teeth comprising the upper edge 24 as it traverses along its slidable path. The serrated teeth of the upper edge 24 are sufficiently angled such that, as the distal portion of the releasable ratchet pawl 28 moves over them from right to left, the distal portion of the releasable ratchet pawl 28 falls into the next gap between adjacent teeth, thereby preventing any opposing movement in the original direction. This allows the V-clamp 26 to be adjusted until it meets the surface of the oral airway device 36 as described above and then be firmly locked into position without any extraneous movements on the part of the user. To release the device 10 from the oral airway device 36, the releasable ratchet pawl 28 is pulled upwards which removes the distal portion from its nested position within the upper edge 24. With the distal portion clear of the serrated teeth of the upper edge 24, the user is then able to slide the V-clamp 26 away from the oral airway device 36. Additionally, the user may manipulate the screw 22 to retract the distal end 34 away from the oral airway device 36 and provide additional clearance therefrom either before or after adjustment of the V-clamp 26.

Figure 4:
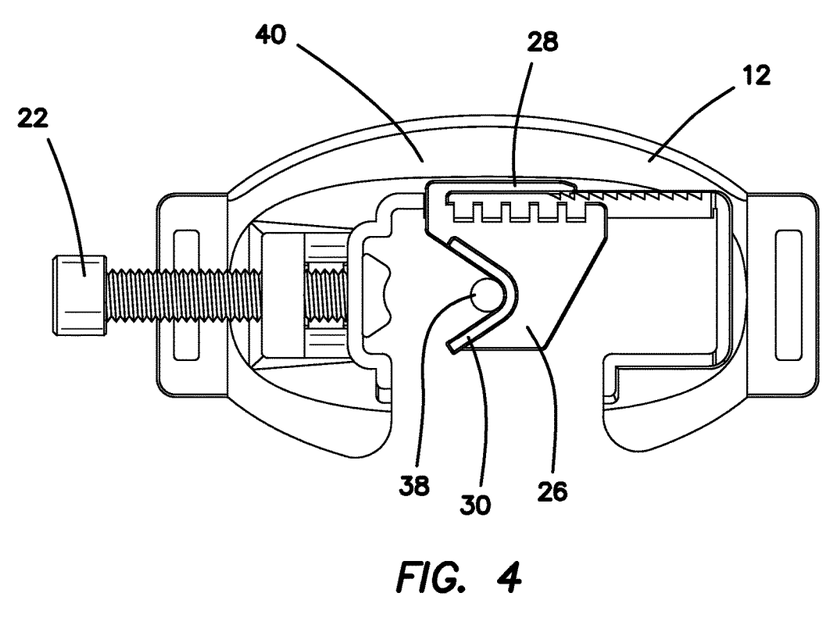
FIG. 4 is a frontal view of the mouthpiece seen in FIG. 1 with a small oral airway device disposed between the V-clamp and the distal end of the thumb screw of the mouthpiece.
Figure 5:
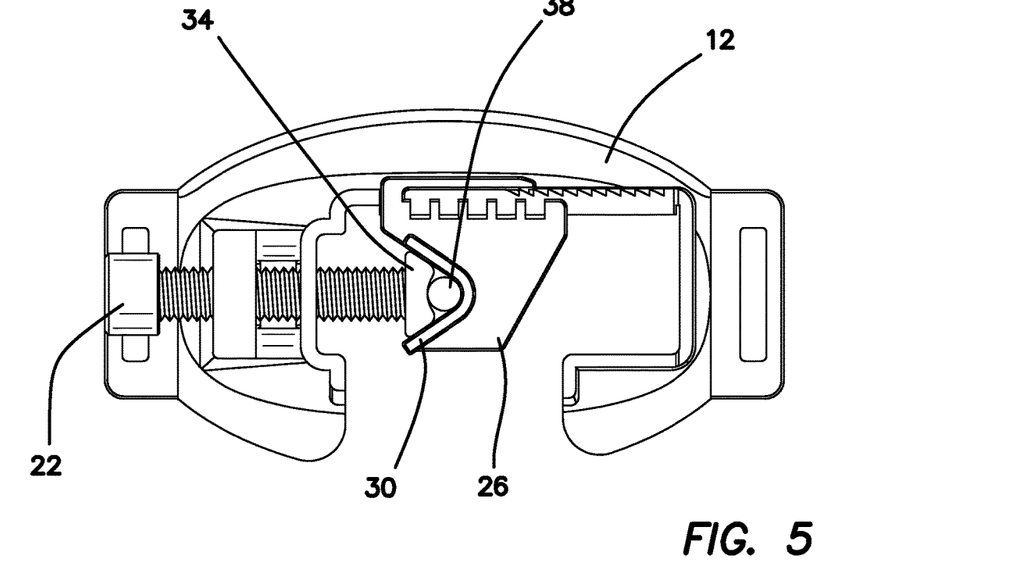
FIG. 5 is a frontal view of the mouthpiece seen in FIG. 4 with the distal end of the thumb screw compressing the small oral airway device against the V-clamp.

In situations where the oral airway device is excessively small, the device 10 may be adjusted to secure the small oral airway device 38 as seen in FIGS. 4 and 5. After the small oral airway device 38 is inserted into the patient and the mask 12 is placed in the proper location as discussed above, the V-clamp 26 is slide as far as possible along the upper edge 24 until it makes contact with stop 40 as seen in FIG. 4. The screw 22 is then rotated which brings the distal end 34 of the screw 34 closer to the small oral airway device 38. The screw 22 is continually manipulated until the distal end 34 either makes contact with the small oral airway device 38 or until the edges of the distal end 34 make surface contact with the inside surface of the V shaped flange as best seen in FIG. 5. The distal end 34 of the screw 22 comprises a substantially angled surface so that it may make full surface contact and nest with the V shaped flange 30 which is angled in the opposing direction relative to the distal end 34 so as to accommodate the distal end 34 of the screw far enough into the triangular or "V" shaped cut out and provide a compressive force against the small oral airway device 38.

Figure 7:
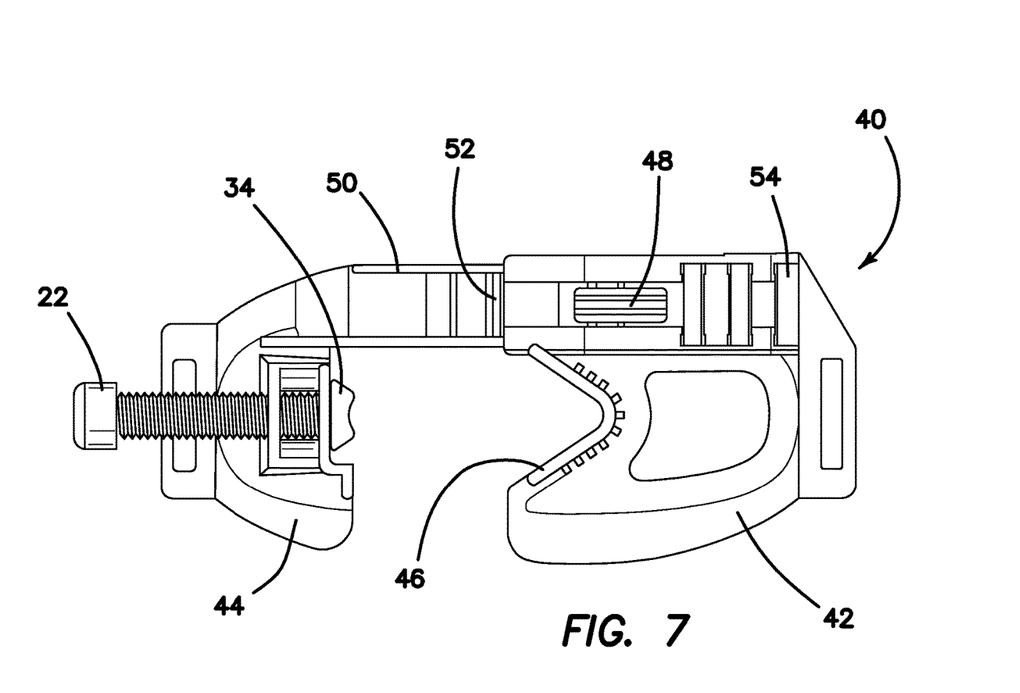
FIG. 7 is a frontal view of an alternative embodiment of the mouthpiece comprising a first portion disposed on a sliding track, the first portion being in the open most position.
Figure 8:
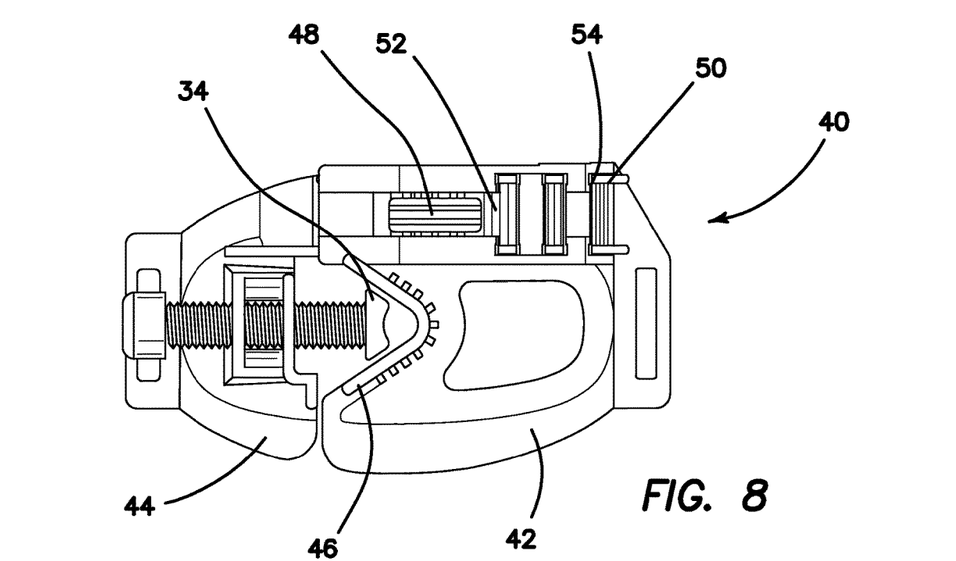
FIG. 8 is a frontal view of the mouthpiece seen in FIG. 7 with the first portion being in the closed position.

An alternative embodiment of the device may be seen in FIGS. 7 and 8 and is denoted generally by reference numeral 40. In this embodiment, the mouthpiece comprises a second portion 44 and a first portion 42. The second portion 44 comprises a ratchet track 50 which comprises a plurality of teeth 52. The first portion 42 comprises a substantially "V" shaped flange 46 on its surface as well as a ratchet pawl 48 and at least one track aperture 54 along its upper most edge.

To operate the device 40, the user inserts an oral airway device into the patient as described above. The user then brings the device over the mouth of the patient with the oral airway device situated between the distal end 34 of the screw 22 and the opening of the "V" shaped flange 46. The user then pushes the two portions of the device 40 together, specifically by sliding the first portion 42 towards the second portion 44. As the first portion 42 moves, the ratchet track 50 on the second portion 44 passes underneath the ratchet pawl 48 disposed on the first portion 42 and enters the first portion 42 through at least one track aperture 54 as seen in FIG. 7. As the ratchet track 50 passes under the ratchet pawl 48, the ratchet pawl 48 makes contact with the plurality of teeth 52. One end of the ratchet pawl 48 comprises a protrusion as is known in the art which interacts with the plurality of teeth 52 and is configured to prevent the relative motion of the ratchet track 50 in the opposing direction away from the first portion 42 of the device 40, much like a ratchet or a zip tie. The leading or distal edge of the ratchet track 50 is inserted through a track aperture 54 to facilitate a close fit between the two portions 42, 44 of the device 40 as the two portions 42, 44 are brought together as seen in FIG. 8. The first portion 42 is continually slid along the ratchet track 50 until the surface edge of the "V" shaped flange 46 makes contact with the oral airway device or until the first portion 42 reaches the end of the ratchet track 50. If after having reached the end of the ratchet track 50 and the first portion 42 has still not made surface contact with the oral airway device, the user may manipulate the screw 22 as discussed above and bring its distal end 34 into contact with the oral airway device or the surface edge of the "V" shaped flange, whichever occurs first. To release the device 40 and remove it from the patient's proximity, the user depresses on the opposing end of the ratchet pawl 48 which brings the protrusion out of the plurality of teeth 52. The user is then able to slide the first portion 42 away from the oral airway device and clear the patient's oral cavity region.

Figure 9:
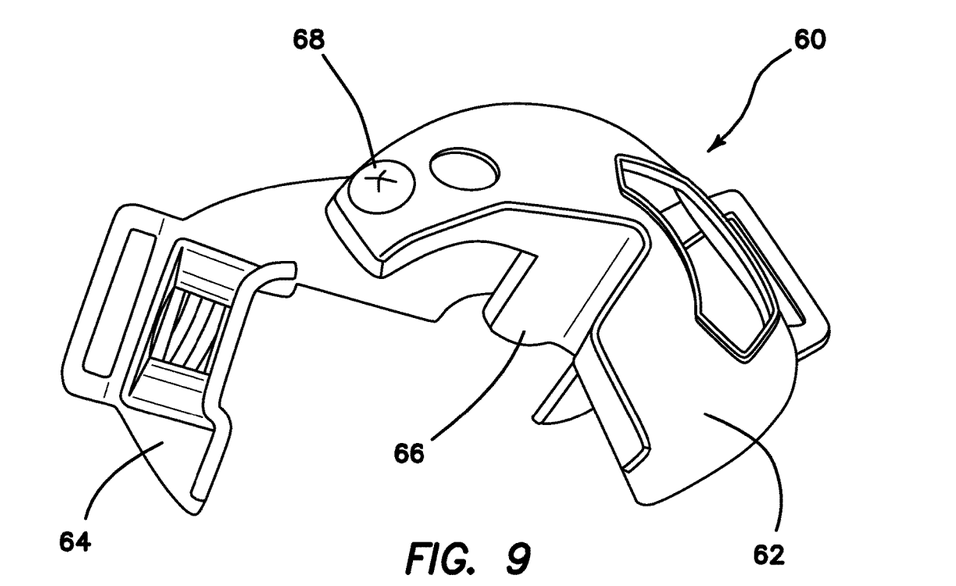
FIG. 9 is a frontal view of an alternative embodiment of the mouthpiece comprising a rotating portion coupled to a fixed portion via a pivot, the rotating portion being in the open most position.
Figure 10:
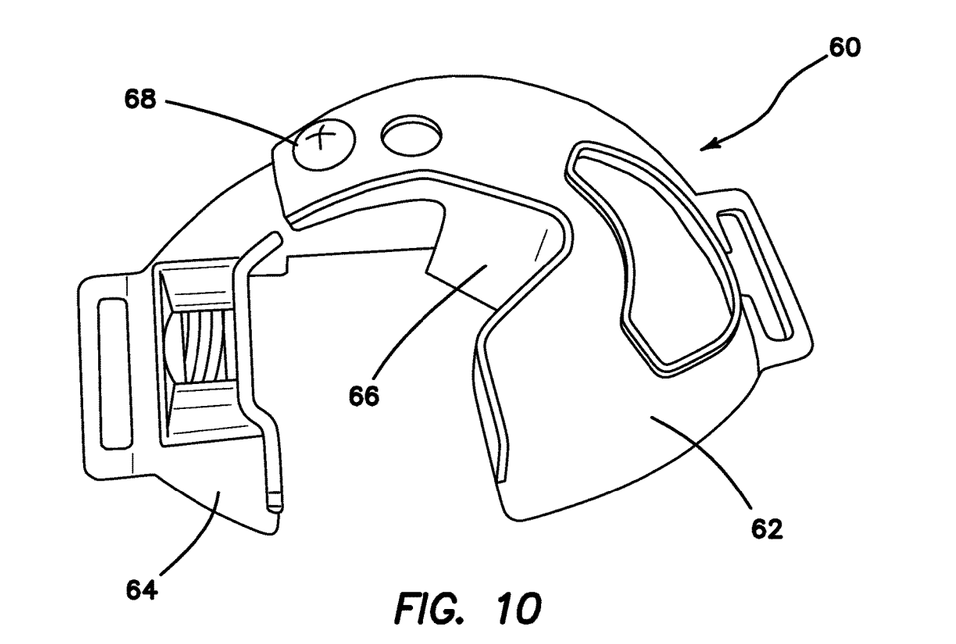
FIG. 10 is a frontal view of the mouthpiece seen in FIG. 9 with the rotating portion being in the closed position.

In yet another embodiment seen in FIGS. 9 and 10, the device is generally denoted by reference numeral 60. In this embodiment, the mouthpiece comprises two portions, specifically a rotating portion 62 and a fixed portion 64. Like the previous embodiments, the rotating portion 62 comprises a substantially "V" shaped flange 66 defined into its surface so as to accommodate a plurality of variously sized and shaped oral airway devices. The rotating portion 62 is coupled to the fixed portion 64 by a pivot 68. In the figures, the pivot 68 is depicted as a screw or bolt, however it is to be expressly understood that other equivalent structures which provide a permanent or temporary means for rotating the portions 62, 64 with respect to one another may be used without departing from the original spirit and scope of the invention.

To operate the device 60, the user inserts an oral airway device into the patient as described above. The user then brings the fixed portion 64 of the device 60 near the mouth of the patient, with the rotating portion 62 rotated upwards with respect to the fixed portion 34 as seen in FIG. 9. With the fixed portion 64 in place adjacent to one side of the oral airway device, the user then rotates the rotating portion 64 in the clockwise direction about the pivot 68 and brings the "V" shaped flange 66 of the rotating portion 64 within close proximity to the opposing side of the oral airway device. The rotating portion 64 may also be rotated until contact with the oral airway device is made via the "V" shaped flange 66, or alternatively, a screw such as described above may be disposed within the fixed portion 64 and be manipulated until the oral airway device is in a fixed, compressed location between the fixed portion 64 and the rotating portion 62. To release, the rotating portion 62 is rotated in the counterclockwise direction until the "V" shaped flange 66 clears the area surrounding the oral airway device. The mouthpiece of the device 60 then removed from the general region of the patient.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

I claim:

1. A device for securing an oral airway device in the oral cavity of a patient comprising:
   a first portion of a mouthpiece having a generally C-shaped body and a threaded bore defined therethrough and an open space defined in the first portion of the mouthpiece to accommodate the oral airway device in the open space, the threaded bore communicating with the open space;
   an adjustable screw threaded into the threaded bore and extending into the open space defined in the first portion of the mouthpiece; and
   a second portion of the mouthpiece including an adjustable clamp opposable the screw, the adjustable clamp slidingly coupled to the C-shaped body and disposed in the open space, and wherein a V-shaped flange is defined in the adjustable clamp.

2. The device of claim 1 where the second portion of the mouthpiece includes a releasable ratchet pawl and where the first portion of the mouthpiece includes a ratchet track having a plurality of ratchet teeth configured to engage the ratchet pawl to limit motion of the second portion of the mouthpiece to one permitted direction relative to the first portion of the mouthpiece, the one permitted relative motion allowing the first and second portions of the mouthpiece to be moved only toward each other to bring the V shaped flange toward the screw extending into the open space, release of the ratchet pawl allowing motion of the second portion of the mouthpiece relative to the first portion of the mouthpiece in an opposite direction to the one permitted direction portion.

3. The device of claim 2 where the first portion of the mouthpiece further comprises a plurality of track apertures, each of which are configured to accommodate a distal end of the ratchet track therethrough.

4. The device of claim 1 where the C-shaped body has an edge with ratchet teeth defined thereon and where the adjustable clamp comprises a releasable ratchet pawl and where the sliding clamp is coupled to the edge of the C shaped body so that the releasable ratchet pawl engages the ratchet teeth defined on the edge as the adjustable clamp traverses the edge.

5. The device of claim 4 where a distal portion of the ratchet pawl and the ratchet teeth are configured to prevent any unpermitted movement of the adjustable clamp when the distal portion of the ratchet pawl and ratchet teeth are in a nested position.

6. The device of claim 1 where the device further comprises:
    a first eyelet and a second eyelet disposed on respective first and second portions of the mouthpiece configured to accommodate a strap used to fix the first and second portions of the mouthpiece over the mouth of the patient; and
    a bite block disposed on a rear surface of the adjustable clamp.

7. A method for securing an oral airway device in a mouth of a patient comprising:
    inserting the oral airway device into the mouth of the patient;
    placing a device comprising a mouthpiece over the mouth of the patient, the oral airway device being disposed within an open space defined in the mouthpiece;
    sliding a clamp coupled to the mouthpiece across the open space, a V-shaped flange defined in the clamp;
    making contact between a first surface of the oral airway device and the V-shaped flange; and
    adjusting a screw disposed in the mouthpiece until contact is made with a second surface of the oral airway device and a compressive force is applied between a distal end of the screw and the clamp.

8. The method of claim 7 where sliding a clamp further comprises:
    ratcheting a distal portion of a releasable ratchet pawl included in the clamp over a plurality of ratchet teeth defined along an edge of the open space; and
    preventing any movement of the clamp along the edge of the open space after contact has been made with the oral airway device.

9. The method of claim 7 where sliding a clamp further comprises:
    moving a ratchet pawl included in the clamp over a plurality of ratchet teeth disposed along a ratchet track coupled to the mouthpiece;
    inserting a distal end of the ratchet track into one of a plurality of track apertures defined in the clamp; and
    preventing any movement of the clamp along the ratchet track after surface contact has been made with the oral airway device.

10. The method of claim 7 further comprising:
    adjusting the fit of the mouthpiece over the mouth of the patient by tightening an adjustable strap coupled to either one of two ends of the mouthpiece;
    inserting a bite block disposed on an opposing surface of the clamp into the oral cavity of the patient; and
    releasing the oral airway device from the mouthpiece by breaking surface contact between the distal end of the screw and the second surface of the oral airway device and between the V-shaped flange of the clamp and the first surface of the oral airway device.

\* \* \* \* \*